(12) United States Patent
Duff (10) Patent No.: US 9,506,639 B1
(45) Date of Patent: Nov. 29, 2016

(54) LIGHTING SYSTEMS AND METHODS

(71) Applicant: Honda Motor Co., Ltd., Minato-ku, Tokyo (JP)

(72) Inventor: Douglas J. Duff, Marysville, OH (US)

(73) Assignee: HONDA MOTOR CO., LTD., Tokyo (JP)

( * ) Notice: Subject to any disclaimer, the term of this patent is extended or adjusted under 35 U.S.C. 154(b) by 17 days.

(21) Appl. No.: 14/804,181

(22) Filed: Jul. 20, 2015

(51) Int. Cl.
| | |
|---|---|
| *F21V 19/00* | (2006.01) |
| *F21V 21/26* | (2006.01) |
| *F21V 21/16* | (2006.01) |
| *F21S 8/04* | (2006.01) |
| *F21W 131/40* | (2006.01) |

(52) U.S. Cl.
CPC .................. *F21V 21/26* (2013.01); *F21S 8/04* (2013.01); *F21V 21/16* (2013.01); *F21W 2131/40* (2013.01)

(58) Field of Classification Search
CPC .......... F21V 21/26; F21V 21/16; F21S 8/04; F21W 2131/40
See application file for complete search history.

(56) References Cited

U.S. PATENT DOCUMENTS

| | | | |
|---|---|---|---|
| 3,375,362 | A | 3/1968 | Klippert |
| 4,651,258 | A | 3/1987 | Davis et al. |
| 4,941,182 | A | 7/1990 | Patel |
| 5,223,306 | A | 6/1993 | Bartow |
| 6,517,216 | B1 | 2/2003 | Cercone et al. |
| 6,588,916 | B2 | 7/2003 | Belair |
| 7,014,338 | B2 | 3/2006 | Pippa et al. |
| 7,591,566 | B2 | 9/2009 | Galke et al. |
| 7,993,030 | B2 | 8/2011 | Galke et al. |
| 8,756,827 | B1 | 6/2014 | Calabro et al. |
| 8,840,272 | B2 | 9/2014 | Manning |
| 2014/0301078 | A1 | 10/2014 | Gordin et al. |

*Primary Examiner* — Tracie Y Green
(74) *Attorney, Agent, or Firm* — Arent Fox LLP (57) ABSTRACT

An apparatus includes a light fixture and a cable operatively coupled to the light fixture. In one aspect, the apparatus also includes an actuator operatively coupled to the cable to draw in or draw out the cable. The apparatus further includes a bar having a first portion pivotably coupled to the light fixture and a second portion pivotably coupled to a support.

20 Claims, 7 Drawing Sheets

LIGHTING SYSTEMS AND METHODS

BACKGROUND

The subject matter disclosed herein relates to visual inspection systems and, more particularly, to lighting systems and methods.

Vehicle inspection areas are typically employed to paint and inspect vehicles. A traditional vehicle inspection area typically includes one or more stationary or fixed lights to illuminate a vehicle in the vehicle inspection area.

SUMMARY

According to one aspect, an apparatus includes a light fixture and an actuator coupled to the light fixture. The actuator is configured to translate and rotate the light fixture to move the light fixture from a first position to a second position. The light fixture in the first position extends from a first plane to a second plane. The light fixture in the second position is positioned outside a space between the first plane and the second plane. The first plane is a first predetermined distance from a support surface in a direction normal to the first plane, and the second plane is a second predetermined distance from the support surface in the direction normal to the first plane.

According to another aspect, a system includes a first array of first light fixtures and a second array of second light fixtures. The system also includes an actuator operatively coupled to the second array of second light fixtures to move the second array of second light fixtures from a first position to a second position. The second array of second light fixtures is offset from the first array of first light fixtures to enable the second light fixtures to interlace the first light fixtures when the second array of second light fixtures moves from the first position to the second position.

According to yet another aspect, an apparatus includes a light fixture and a cable operatively coupled to the light fixture. The apparatus also includes an actuator operatively coupled to the cable to at least one of draw in or draw out the cable. The apparatus further includes a bar having a first portion pivotably coupled to the light fixture and a second portion pivotably coupled to a support.

According to another aspect, a method includes illuminating an area via a first light fixture positioned over a portion of the area. The method also includes suspending a second light fixture in a first position above a support surface via a cable and a bar pivotably coupled to the second light fixture. The method further includes drawing in the cable via an actuator to raise and rotate the second light fixture from the first position to a second position. The second light fixture in the second position is positioned over a portion of the area without obstructing light generated via the first light fixture and directed toward the support surface.

BRIEF DESCRIPTION OF THE DRAWINGS

Like reference numerals are used herein to refer to like components and/or systems.

DETAILED DESCRIPTION

Example lighting systems are disclosed herein. The exemplary lighting systems disclosed herein may be used to illuminate a vehicle in an inspection booth. In some embodiments, a lighting system may include a first array of first light fixtures and a second array of second light fixtures. The first array of first light fixtures may be disposed over the vehicle and oriented substantially horizontal to a support surface, such as a floor of the inspection booth. The second array of second light fixtures may be disposed adjacent a side of the vehicle and oriented substantially vertical to the floor of the inspection booth. As a result, the second light fixtures may physically obstruct one or more areas in the inspection booth and/or visually obstruct a person's field of view to the vehicle.

The exemplary lighting systems disclosed herein may include an actuator operatively coupled to the second array of second light fixtures to move the second array of second light fixtures from a first position, such as a fully lowered position adjacent the side of the vehicle, to a second position, such as a fully raised position over the vehicle. For example, the actuator may include a cable operatively coupled to the second array of second light fixtures to lift the second light fixtures relative to the floor. In some embodiments, one or more bars is pivotably coupled to one or more fixed supports and the second array of second light fixtures to guide a rotational path of the second light fixtures as the second light fixtures move between the fully lowered position and the fully raised position. For example, as the cable raises the second light fixtures, the one or more bars push or pull the second light fixtures to rotate the second light fixtures. In some embodiments, when the second light fixtures are in the fully raised position, the second light fixtures are disposed above, at a same height, and/or intertwined or meshed with the first light fixtures. As a result, in some such embodiments, the second light fixtures in the fully raised position do not obstruct light generated via the first light fixtures and directed towards the floor and/or the vehicle.

Figure 1:
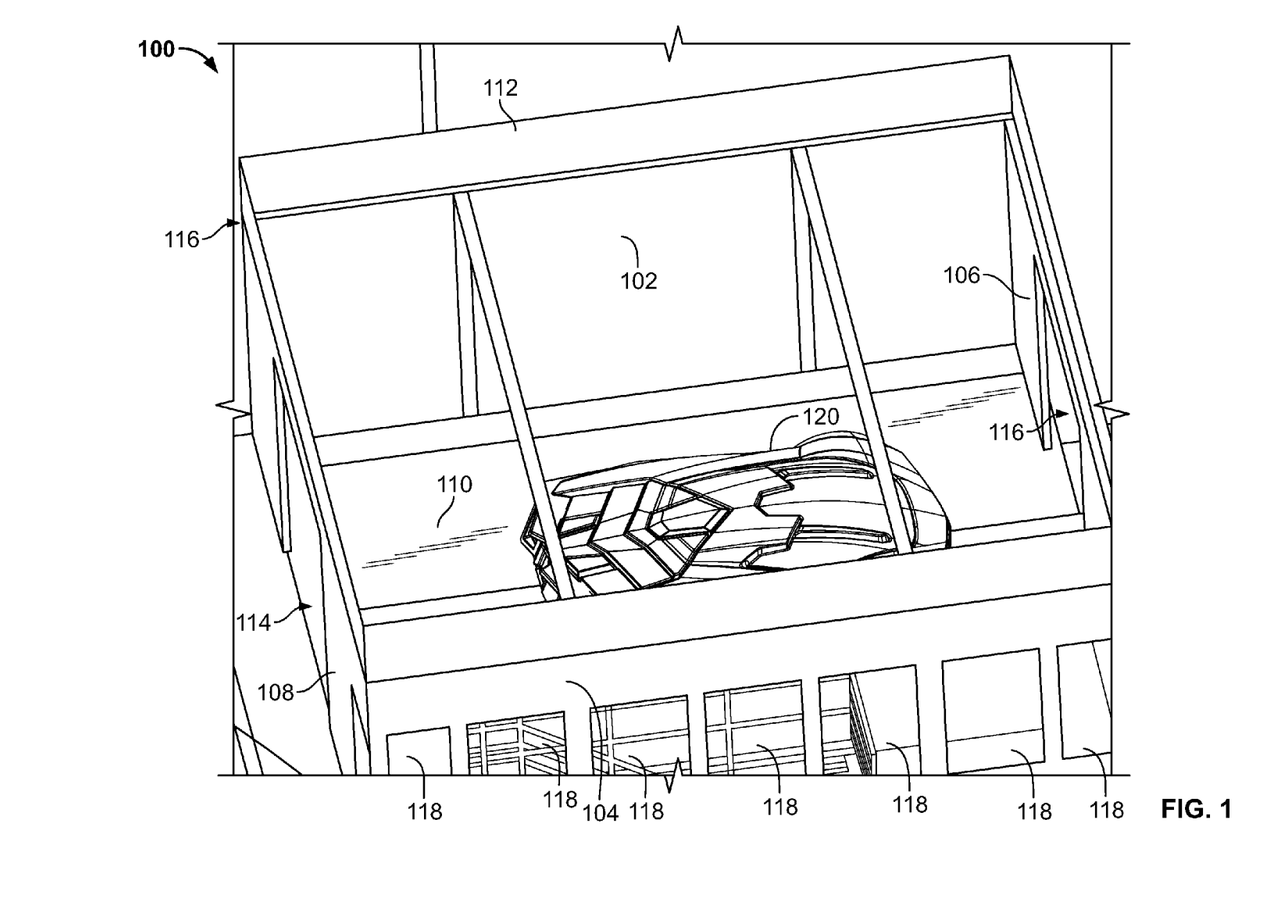
FIG. 1 is a top, perspective cutaway view of an exemplary inspection booth disclosed herein.

FIG. 1 is a cutaway view of an exemplary inspection booth 100 disclosed herein. Although the following embodiments are described in conjunction with the inspection booth 100, the lighting systems disclosed herein may be employed in any suitable building, room, enclosure, and/or area. The inspection booth 100 of FIG. 1 includes a first wall 102, a second wall 104, a third wall 106, a fourth wall 108, a support surface or floor 110, and a ceiling 112. A portion of the ceiling 112 is not shown in FIG. 1 to enable an interior of the inspection booth 100 to be visible in FIG. 1. In the embodiment of FIG. 1, the first wall 102 is opposite the second wall 104. The third wall 106 of FIG. 1 is opposite the fourth wall 108. The fourth wall 108 includes a first opening or vehicle ingress 114 of the inspection booth 100. The third wall 106 includes a second opening or vehicle egress 116 of the inspection booth 100. The vehicle ingress 114 and/or the vehicle egress 116 may be closed and/or sealed via, for example, a first door and a second door, respectively.

In the embodiment shown in FIG. 1, the second wall 104 includes a plurality of windows 118. A vehicle 120 is positioned inside the inspection booth 100 of FIG. 1. As a result, a person outside of the inspection booth 100 may view the vehicle 120 via one or more of the windows 118 during an inspection of the vehicle. In this embodiment, the vehicle 120 is an automobile. In other embodiments, the vehicle 120 is another type of vehicle such as, for example, a truck, a bus, a van, a go-cart, a motorcycle, a scooter, a bicycle, an all-terrain vehicle ("ATV"), a heavy equipment vehicle (e.g., a bulldozer, a crane, a combine, a tractor, a forklift, an asphalt paver, and/or any other heavy equipment vehicle), and/or any other type of vehicle. In other embodiments, one or more painted components, articles, and/or parts (e.g., a fender, a body panel, a helmet, etc.) are positioned inside the inspection booth 100 of FIG. 1. As described in greater detail below, the inspection booth 100 of FIG. 1 facilitates visual inspection of paint of the vehicle 120 and/or one or more painted components, articles, and/or parts.

Figure 2:
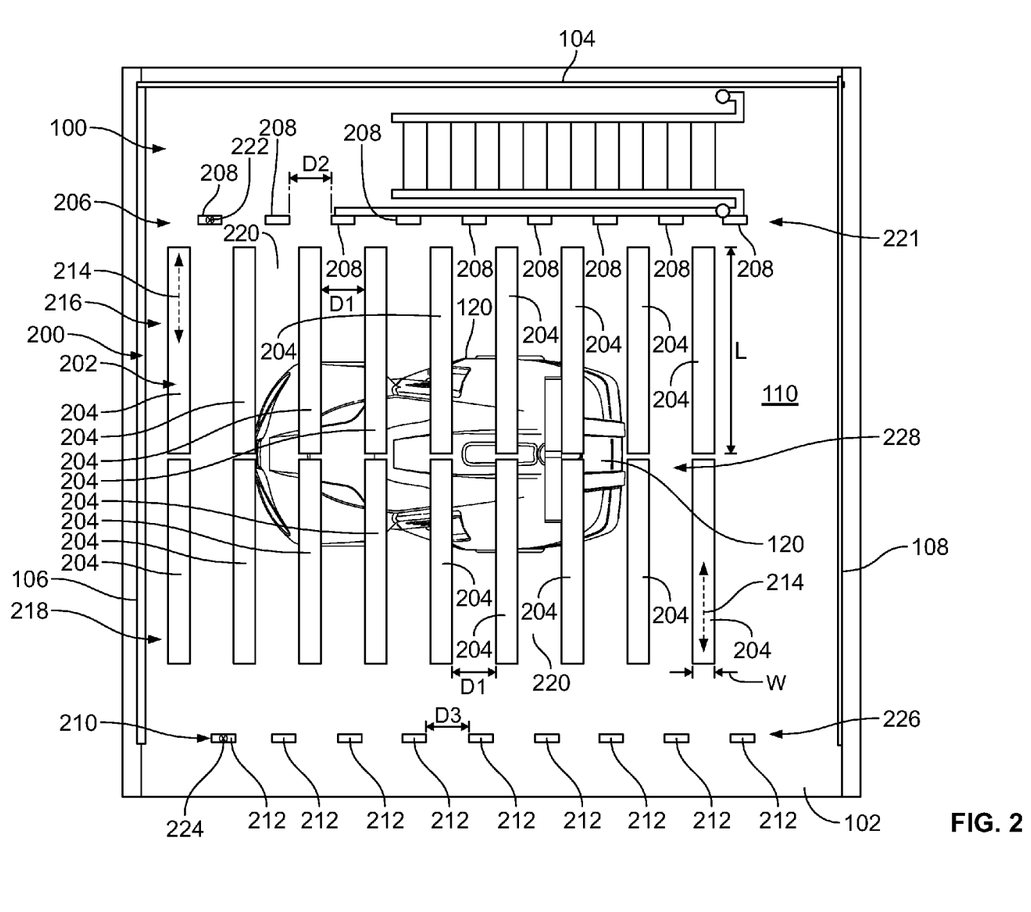
FIG. 2 is a top, cutaway view of the exemplary inspection booth of FIG. 1.

FIG. 2 is a top, cutaway view of the exemplary inspection booth 100 of FIG. 1 including an exemplary lighting system 200 disclosed herein. In the embodiment of FIG. 2, the lighting system 200 includes a first array 202 of first light fixtures 204, a second array 206 of second light fixtures 208, and a third array 210 of third light fixtures 212. Each of the first light fixtures 204, the second light fixtures 208, and the third light fixtures 212 has a suitable length L, such a length L of about eight feet and a suitable width W, such as a width W of about 10 inches. However, all of the above-mentioned dimensions are merely examples and, thus, other dimensions may be employed without departing from the scope of this disclosure.

In the embodiment of FIG. 2, the first array 202 of the first light fixtures 204 is adjacent the ceiling 112 (FIG. 1). Thus, the first array 202 of the first light fixtures 204 is disposed above or over the vehicle 120. For example, the first light fixtures 204 may be coupled to (e.g., suspended from) the ceiling 112 such that each of the first light fixtures 204 are disposed above the floor 110 by a suitable distance, such as about eight feet in a direction normal to the floor. In other embodiments, the first light fixtures 204 are disposed at other distances above the floor 110. In some embodiments, the first light fixtures 204 generate light and direct the light toward the floor 110 to illuminate the vehicle 120.

In the embodiment shown in FIG. 2, longitudinal axes 214 of each of the first light fixtures 204 extend toward the first wall 102 and the second wall 104. The longitudinal axes 214 of the first light fixtures 204 are oriented substantially horizontal in the embodiment shown and, thus, parallel to the floor 110. As a result, the first light fixtures 204 of FIG. 2 are substantially parallel to each other. In other embodiments, the first light fixtures 204 may be oriented in other ways. In the illustrated embodiment, the first array 202 includes a suitable number of the first light fixtures 204, such as eighteen of the first light fixtures 204. In this particular embodiment, a first nine of the first light fixtures 204 are arranged in a first row 216, and a second nine of the first light fixtures 204 are arranged in a second row 218 juxtaposing the first row 216. Each of the first light fixtures 204 in the first row 216 are spaced apart from an adjacent one of the first light fixtures 204 in the first row 216 by a distance D1, and each of the first light fixtures 204 in the second row 218 are spaced apart from an adjacent one of the first light fixtures in the second row 218 by the distance D1. As a result, the first array 202 of the first light fixtures 204 includes a plurality of spaces or lanes 220 between the first light fixtures 204. In other embodiments, the first array 202 includes other suitable numbers of the first light fixtures 204 and/or the first light fixtures 204 are arranged in other suitable ways.

In FIG. 2, the second array 206 of the second light fixtures 208 are disposed on a first side of the inspection booth 100 adjacent the second wall 104. Thus, the second light fixtures 208 are positionable between the second wall 104 and the vehicle 120. The second light fixtures 208 of FIG. 2 are oriented substantially parallel to each other. In the illustrated embodiment, the second array 206 of the second light fixtures 208 is in a first position. In some embodiments, the first position is a fully lowered position. When the second array 206 is in the first position, longitudinal axes 222 of the second light fixtures 208 are oriented substantially perpendicular to the floor 110 and, thus, extend into and out of the page in the orientation of FIG. 2. Thus, when the second array 206 is in the first position, the second light fixtures 208 direct light substantially toward the vehicle 120 and the first wall 102 to illuminate the vehicle 120. In other embodiments, the second light fixtures 208 are oriented in other ways when the second array 206 is in the first position.

The second array 206 includes nine of the second light fixtures 208 arranged in a third row 223. In other embodiments, the second array 206 includes other suitable numbers of the second light fixtures 208 (e.g., 1, 2, 3, 4, 5, 6, . . . , 10, etc.). Each of the second light fixtures 208 are spaced apart from an adjacent one of the second light fixtures 208 in the third row 223 by a distance D2. In other embodiments, the second light fixtures 208 are oriented and/or arranged in other ways. In the embodiment of FIG. 2, the second array 206 of the second light fixtures 208 is offset from the first array 202 of the first light fixtures 204. For example, in the embodiment of FIG. 2, each of the second light fixtures 208 is aligned with one of the lanes 220 of the first array 202. Thus, as described in greater detail below, when the second array 206 of the second light fixtures 208 is raised and rotated to a second position, such as the fully raised position, the offset between the first light fixtures 204 and the second light fixtures 208 enable the second light fixtures 208 and the first light fixtures 204 to interlace or mesh and be positioned in a planar configuration.

The third array 210 of the third light fixtures 212 is disposed on a second side of the inspection booth 100 adjacent the first wall 102. In the embodiment of FIG. 2, longitudinal axes 224 of the third light fixtures 212 are oriented substantially perpendicular to the floor 110 and, thus, extend into and out of the page in the orientation of FIG. 2. As a result, the third light fixtures 212 are oriented substantially parallel to each other. Thus, the third light fixtures 212 direct light substantially toward the vehicle 120 and the second wall 104 to illuminate the vehicle 120. In this embodiment, the third array 210 includes nine of the third light fixtures 212 arranged in a fourth row 226. Each of the third light fixtures 212 are spaced apart from an adjacent one of the third light fixtures 212 in the fourth row 226 by a distance D3. In the embodiment of FIG. 2, the first distance D1, the second distance D2, and the third distance D3 are substantially a same or equal distance. In other embodiments, the first distance D1, the second distance D2, and/or the third distance D3 are different distances. In other embodiments, the third light fixtures 212 are oriented and/or arranged in other ways.

In this embodiment, the first light fixtures 204, the second light fixtures 208, and/or the third light fixtures 212 generate light to illuminate a first area 228 within the inspection booth 100. In the embodiment of FIG. 2, the first area 228 includes a space between the second array 206 and the third array 210 and between the floor 110 and the first array 202. The vehicle 120 of FIG. 2 is positioned in the first area 228.

Figure 3:
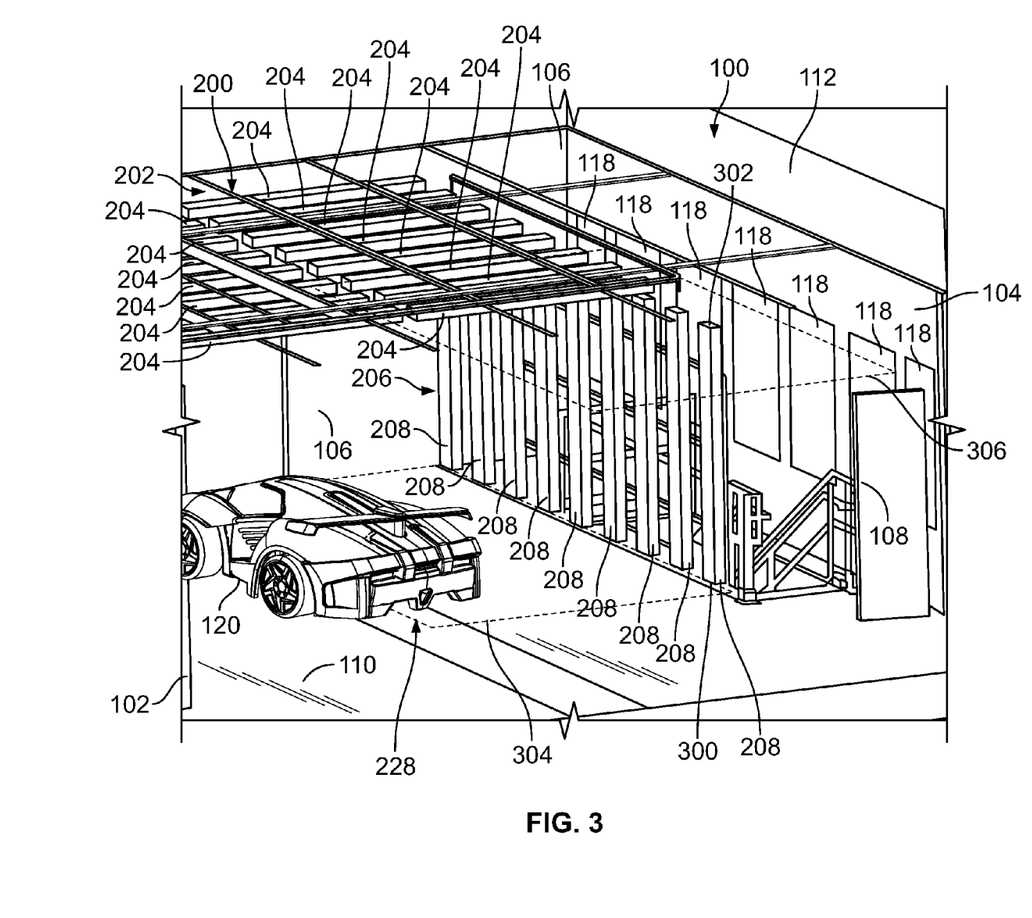
FIG. 3 is a rear, perspective cutaway view of the exemplary inspection booth of FIG. 2 showing an exemplary lighting system disclosed herein.

FIG. 3 is a perspective, cutaway view of the inspection booth 100 of FIGS. 1 and 2 employing the exemplary lighting system 200 of FIG. 2. In the embodiment of FIG. 3, the second array 206 is in the first position. When the second array 206 is in the first position, respective first ends 300 of the second light fixtures 208 are disposed on (e.g., in contact with) or adjacent the floor 110 and respective second ends 302 of the second light fixtures 208 are adjacent the first array 202 of the first light fixtures 204 and/or the ceiling 112. For example, in the embodiment of FIG. 3, the first ends 300 of the second light fixtures 208 are spaced apart from the floor 110 by about four inches in a direction normal to the floor 110. The second ends 302 of the second light fixtures 208 are spaced apart from the floor 110 by about one hundred inches in the direction normal to the floor 110. Thus, when the second array 206 is in the first position, the second light fixtures 208 extend from a first horizontal plane 304 to a second horizontal plane 306, where the first horizontal plane 304 is at a suitable distance, such as four inches from the floor 110, and the second horizontal plane 306 is at a suitable distance, such as one hundred inches from the floor 110, in a direction normal to the first horizontal plane 304 and the second horizontal plane 306. Thus, the second light fixtures 208 of FIG. 3 extend through all horizontal planes between the first horizontal plane 304 and the second horizontal plane 306 such as, for example, horizontal planes spaced apart from the floor 110 in the direction normal to the plane(s) by distances of one inch, one foot, two feet, three feet, four feet, five feet, six feet, seven feet, and/or other distances. The above-mentioned dimensions are merely examples and, thus, other suitable dimensions may be used without departing from the scope of this disclosure. In some embodiments, when the second array 206 is in the first position, the second light fixtures 208 generate light to illuminate the first area 228. In the embodiment of FIG. 2, the second light fixtures 208 direct the light toward the vehicle 120 and the first wall 102.

Figure 4:
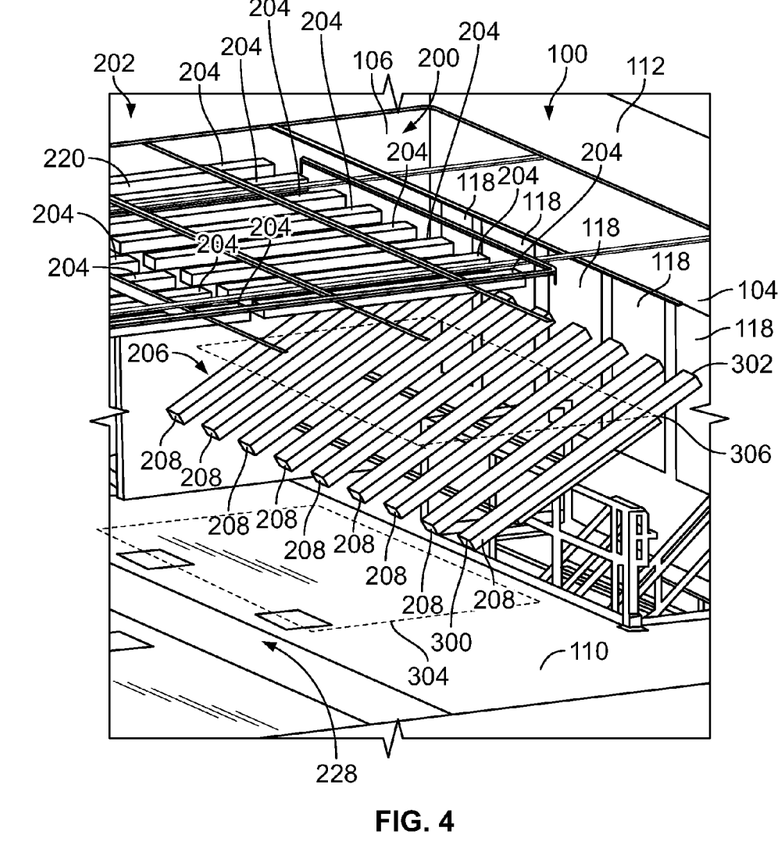
FIG. 4 is a rear, perspective cutaway view of the lighting system of FIG. 3 showing an array of light fixtures being raised from a first position to a second position.
Figure 6:
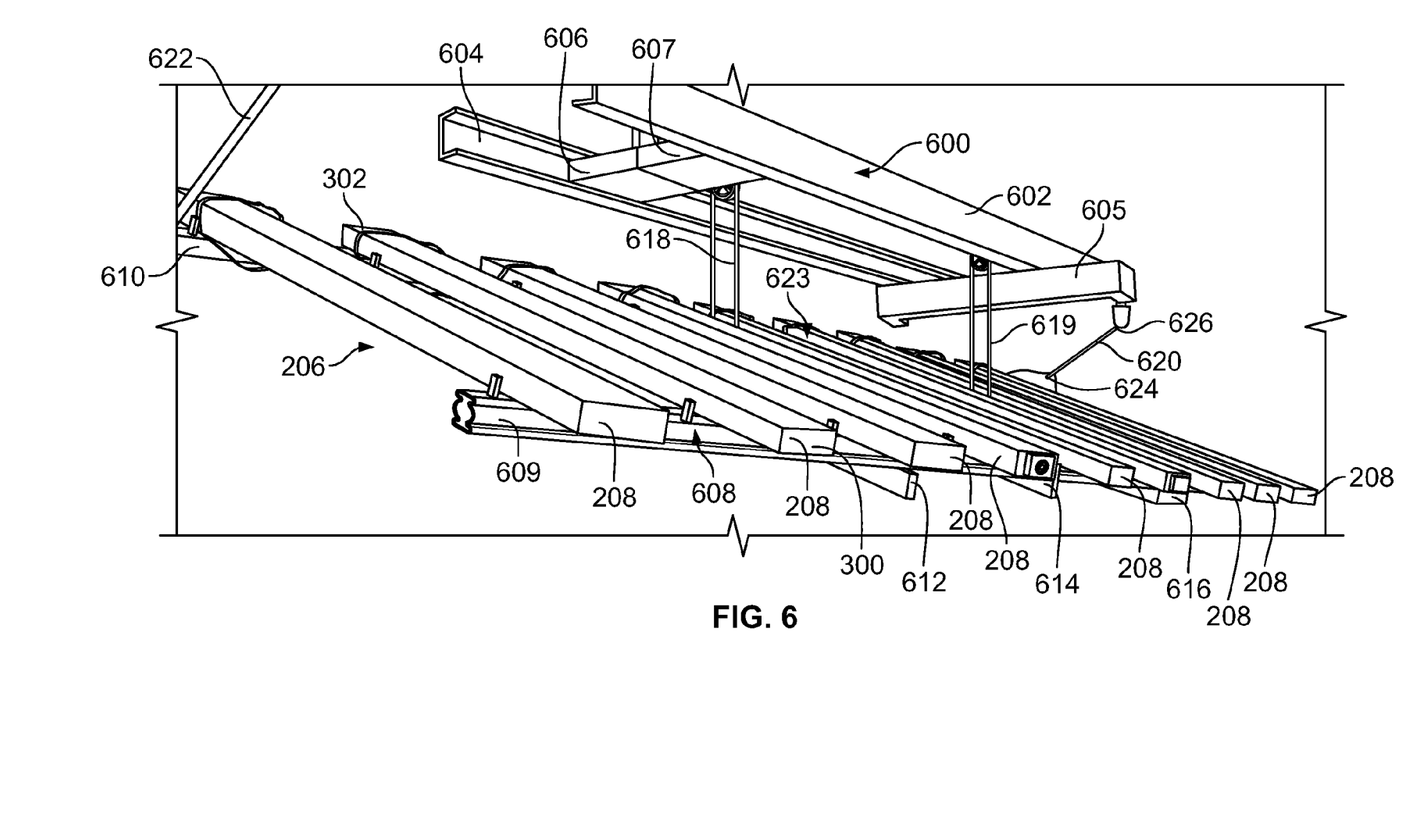
FIG. 6 is a perspective view of an actuator and the array of the light fixtures of FIGS. 3-5.

FIG. 4 is a perspective, cutaway view of the inspection booth 100 of FIGS. 1-3. The vehicle 120 of FIGS. 1-3 is not shown in FIG. 4. In FIG. 4, the second array 206 of the second light fixtures 208 is disposed in an intermediate or third position between the first position and the second position. In the embodiment of FIG. 4, an actuator 600, as shown in FIG. 6, rotates and translates the second array 206 of the second light fixtures 208 to move the second array 206 of the second light fixtures 208 from the first position to the second position and from the second position to the first position. When the actuator 600 moves the second light fixtures 208 from the first position towards the second position, the first ends 300 of the first light fixtures 308 move upwards (e.g., toward the first wall 102 and toward the ceiling 112), and the second ends 302 move downwards (e.g., toward the second wall 104 and toward the floor 110).

In some embodiments, the second array 206 of the second light fixtures 208 moves from the first position to the second position while the vehicle 120 is in the inspection booth 100 to enable one or more persons located outside of the inspection booth 100 to view the vehicle 120 through one or more of the windows 118 without the second array 206 of the second light fixture 208 obstructing a line of sight of the one or more persons to the vehicle 120. In some embodiments, the actuator 600 rotates and translates the second array 206 of the second light fixtures 208 to move the second array 206 of the second light fixtures 208 around the vehicle 120 and/or other objects and/or structures (e.g., a handrail, a wall, etc.). For example, in some embodiments, when the second array 206 of the second light fixtures 208 is in the first position, the second array 206 of the second light fixtures 208 is in close proximity to the vehicle 120 and/or one or more objects and/or structures. Therefore, the actuator 600 translates and rotates the second array 206 of the second light fixtures 208 to enable the second array 206 of the second light fixtures 208 to be raised and/or lowered without contacting with the vehicle 120 and/or the one more objects and/or structures. Thus, in some embodiments, the combination of translation and rotation of the second array 206 of the second light fixtures 208 enables the inspection booth 100 to be more compact than if the second array 206 of the second light fixtures 208 only rotated or only translated and/or enables the second array 206 of the second light fixtures 208 to be raised and/or lowered while the vehicle 120 is in the inspection booth 100.

Figure 5:
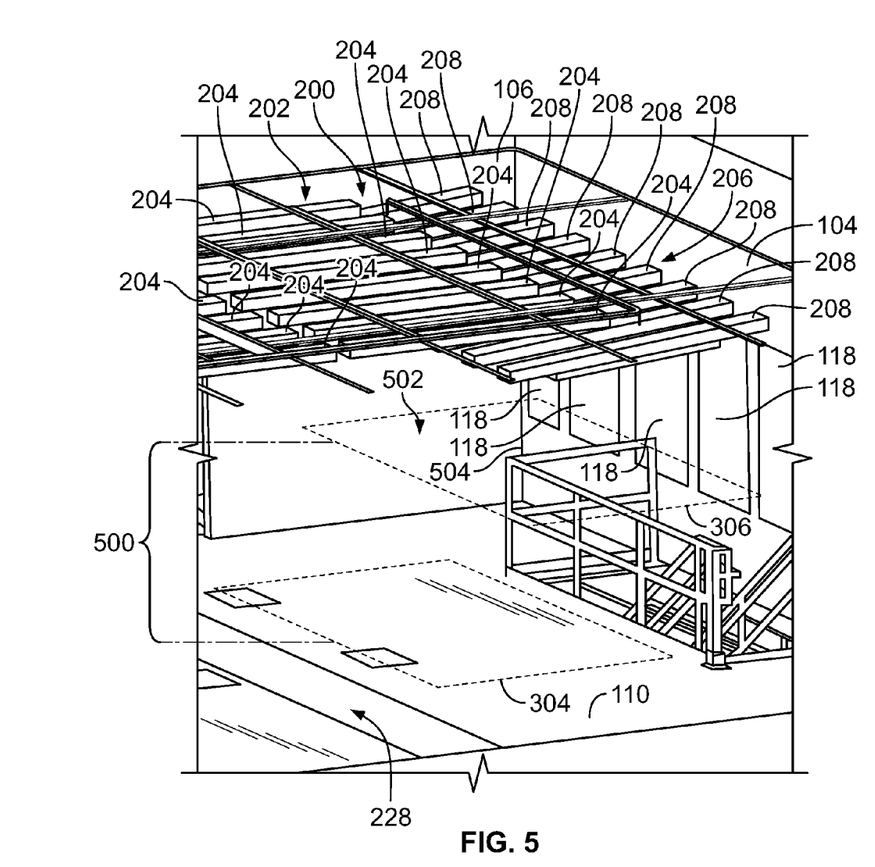
FIG. 5 is a rear, perspective view of the lighting system of FIGS. 3 and 4 showing the array of the light fixtures disposed in the second position.

FIG. 5 is a perspective, cutaway view of the inspection booth 100 of FIGS. 1-4 showing the second array 206 of the second light fixtures 208 moving toward the second position. The second light fixtures 208 in the second position are outside (i.e., above) a space 500 between the first horizontal plane 304 and the second horizontal plane 306. In some embodiments, the second light fixtures 208 are interlaced or meshed with the first light fixtures 204 when the second array 206 is in the second position. As described herein, the second light fixtures 208 are interlaced or meshed with the first light fixtures 204 when one or more portions of the second light fixtures 208 (e.g., the first ends 300) are disposed in one or more of the lanes 220 of the first array 202 of the first light fixtures 204. In some embodiments, the second light fixtures 208 in the second position are substantially horizontal and/or oriented substantially parallel to the floor 110. In some embodiments, the second light fixtures 208 are disposed above the first light fixtures 204 relative to the floor 110 when the second array 206 is in the second position. Thus, in some such embodiments, the second light fixtures 208 mesh and then unmesh with the first light fixtures 204 as the second light fixtures 208 pass into and through the lanes 220 as the second light fixtures 208 move from the first position to the second position. In other embodiments, the second light fixtures 208 in the second position are oriented and/or configured in other ways.

In some embodiments, when the second array 206 is in the second position, the second light fixtures 208 do not obstruct light generated via the first light fixtures 204 and directed towards the floor 110 and/or the vehicle 120. In some embodiments, the second light fixtures 208 do not generate light when the second array 206 is in the second position. Thus, only the first light fixtures 204 and/or the third light fixtures 212 may illuminate the first area 228 when the second array 206 is in the second position.

In the embodiment of FIG. 5, when the second array 206 is in the second position, the second light fixtures 208 do not block or obstruct the one or more fields of view of the vehicle 120 (FIGS. 1-3) via the windows 118 when the vehicle 120 is positioned inside the inspection booth 100. As a result, a person positioned outside of the inspection booth 100 may have an unobstructed field of view to the vehicle 120 via one or more of the windows 118. In the shown embodiment, a second area 502 adjacent a corner 504 of the second wall 104 and the third wall 108 is accessible to a person when the second array 206 is in the second position.

FIG. 6 shows an exemplary actuator 600, which may be used to implement the lighting system 200 of FIGS. 2-5. In the embodiment of FIG. 6, the actuator 600 includes a first support 602 and a second support 604. The first support 602 and the second support 604 may be coupled to one or more structural supports 605 of the inspection booth 100. In some embodiments, the actuator 600 includes a motor 606 operatively coupled to a winch 607. In some embodiments, the actuator 600 includes one or more additional and/or alternative components. When the actuator 600 is employed in the inspection booth 100 of FIGS. 1-5, the actuator 600 may be disposed within the ceiling 112 of the inspection booth 100, above a ceiling of the inspection booth 100, on a roof of the inspection booth 100, and/or in any other suitable location. In some such embodiments, the actuator 600 may suspend the second array 206 of the second light fixtures 208 inside the inspection booth 100 and below the ceiling 112 and above the floor 110.

The second array 206 of the second light fixtures 208 includes a frame 608 to support the second light fixtures 208. In the embodiment of FIG. 6, the frame 608 includes a first beam 609 adjacent the first ends 300 of the second light fixtures 208. The frame 608 of FIG. 6 also includes a second beam 610 adjacent the second ends 302 of the second light fixtures 208. Each of the second light fixtures 208 is coupled to the first beam 609 and the second beam 610. In the embodiment shown in FIG. 6, the frame 608 further includes a third beam 612, a fourth beam 614, and a fifth beam 616. The third beam 612, the fourth beam 614, and the fifth beam 616 are each coupled to the first beam 609 and the second beam 610. In the embodiment of FIG. 6, the third beam 612, the fourth beam 614, and the fifth beam 616 are transverse to the first beam 609 and the second beam 610. In some embodiments, the frame 608 includes any suitable number of beams (e.g., 1, 2, 3, 4, 5, 6, etc.) and/or the beams 609, 610, 612, 614, 616 are configured in other suitable ways.

The frame 608 of FIG. 6 is coupled to the actuator 600 via a first cable 618, a second cable 619, a first bar 620, and a second bar 622. In the embodiment of FIG. 6, the actuator 600 draws in (e.g., spools) or draws out (e.g., unspools) the first cable 618 and/or the second cable 619 to raise or lower, respectively, the second light fixtures 208. In some embodiments, one or more pulleys (not shown) may be coupled to the fourth beam 612, and the first cable 618 and the second cable 619 may be operatively coupled to the pulleys to support and/or suspend the second array 206 of the second light fixtures 208 above the floor 110 (FIGS. 1-5). In some embodiments, the first cable 618 and the second cable 619 are coupled to the fourth beam 614 at positions spaced apart from and substantially equidistant from a centroid and/or a center of mass 623 of the second array 206, as shown in FIG. 6 for example. In other embodiments, the first cable 618 and/or the second cable 619 are coupled to the frame 608 at other suitable locations and/or in other suitable ways. In other embodiments, the second array 206 of the second light fixtures 208 includes other numbers of cables (e.g., 1, 3, 4, etc.) operatively coupled to the actuator 600.

The first bar 620 and the second bar 622 are pivotably coupled to a stationary or fixed support such as, for example, the second beam 610, the structural support 605 of the inspection booth 100, and/or any other suitable support. For example, a first end 624 of the first bar 620 may be pivotably coupled to the second beam 610, and a second end 626 of the first bar 620 may be pivotably coupled to the structural support 605. In the embodiment of FIG. 6, the second bar 622 is a mirror image of the first bar 620. Thus, the foregoing description of the first bar 620 is applicable to the second bar 622. Therefore, to avoid redundancy, the second bar 622 is not separately described herein.

The first cable 618 and the second cable 619 are spaced apart from the first bar 620 and the second bar 622 to enable the first bar 620 and the second bar 622 to rotate the second array 206 of the second light fixtures 208 when the actuator 600 draws in or draws out the first cable 618 and/or the second cable 619. For example, in the embodiment of FIG. 6, when the actuator 600 raises or lowers the second array 206 of the second light fixtures 208 via the first cable 618 and/or the second cable 619, the first bar 620 and the second bar 622 apply force to the second beam 610 to rotate the second array 206 of the second light fixtures 208. For example, when the actuator 600 raises the second array 206 from the first position to the second position, the first bar 620 and the second bar 622 push the second beam 610 adjacent the second ends 302 of the second light fixtures 208. As a result, in this embodiment, the second array 206 of the second light fixtures 208 rotates from a substantially vertical orientation toward a substantially horizontal orientation. When the actuator 600 lowers the second array 206 of the second light fixtures 208 from the second position to the first position, the first bar 620 and the second bar 622 pull the second beam 610 adjacent the second ends 302 of the second light fixtures 208. As a result, the second array 206 of the second light fixtures 208 rotates from the substantially vertical orientation toward the substantially horizontal orientation in this embodiment. Thus, the first bar 620 and the second bar 622 guide a rotational path of the second array 206 of the second light fixtures 208.

Figure 7:
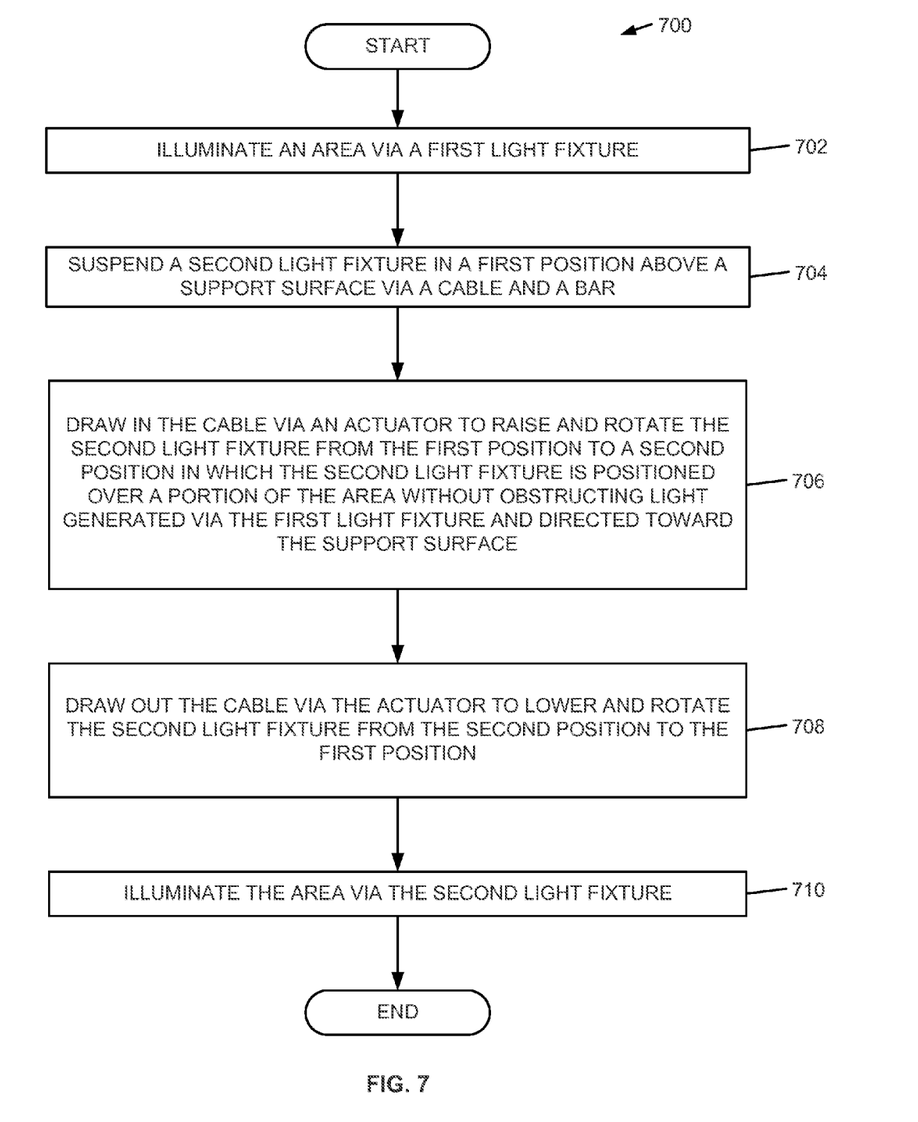
FIG. 7 is a flowchart representative of an exemplary method disclosed herein.

A flowchart representative of an exemplary method 700 to illuminate an area such as, for example, the first area 228 of the inspection booth 100 is shown in FIG. 7. Although the method 700 is described with reference to the flowchart of FIG. 7, other methods of implementing the embodiments disclosed herein may be used. For example, the order of the blocks may be different, and/or some of the blocks may be different, eliminate, or combined.

The method 700 of FIG. 7 begins when the first light fixtures 204 illuminate the first area 228 (block 702). The first light fixtures 204 are positioned over the first area 228. The first cable 618, the second cable 619, the first bar 620, and the second bar 622 suspend the second light fixtures 208 in the first position above the support surface 110 (block 704). In some embodiments, the first cable 618, the second cable 619, the first bar 620, and the second bar 622 suspend the second light fixtures 208 in a substantially vertical orientation when the first light fixtures 208 are in the first position. The actuator 600 draws in the first cable 618 and/or the second cable 619 to raise and rotate the second light fixtures 208 from the first position to the second position (block 706). When the second light fixtures 208 are in the second position, the second light fixtures 208 are positioned over a portion of the first area 228 without obstructing light generated by the first light fixtures 208 and directed toward the support surface 110. For example, the second light fixtures 208 may be positioned above and/or intertwined with the first light fixtures 204 such that the second light fixtures 208 are not positioned between the first light fixtures 204 and the support surface 110. In some embodiments, the second light fixtures 208 in the second position are suspended in a substantially horizontal orientation. In some embodiments, when the second light fixtures 208 are in the second position, the second light fixtures 208 do not generate light. The actuator 600 draws out the first cable 618 and/or the second cable 619 to lower and rotate the second light fixtures 208 from the second position to the first position (block 708). The second light fixtures 208 illuminate the first area 228 (block 710). In some embodiments, the first light fixtures 204 and the third light fixtures 212 also illuminate the first area 228. As a result, the lighting system 200 facilitates visual inspection of the vehicle 120.

The foregoing description of embodiments and examples has been presented for purposes of illustration and description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent devices by those of ordinary skill in the art. Rather, it is hereby intended that the scope be defined by the claims appended hereto. Additionally, the features of various implementing embodiments may be combined to form further embodiments. The word "exemplary" is used herein to mean serving as an example, instance, or illustration. Any aspect or embodiment described herein as "exemplary" is not to be construed as preferred or advantageous over other aspects or embodiments.

What is claimed is:

1. An apparatus, comprising:
   a light fixture; and
   an actuator coupled to the light fixture, the actuator configured to translate and rotate the light fixture to move the light fixture from a first position to a second position, the light fixture in the first position extending from a first plane to a second plane, the light fixture in the second position positioned outside a space between the first plane and the second plane, wherein the first plane is a first predetermined distance from a support surface in a direction normal to the first plane, and the second plane is a second predetermined distance from the support surface in the direction normal to the first plane.

2. The apparatus of claim 1, wherein a longitudinal axis of the light fixture in the first position is substantially vertical.

3. The apparatus of claim 2, wherein the longitudinal axis of the light fixture in the second position is substantially horizontal.

4. The apparatus of claim 1, further comprising a cable operatively coupled to the actuator and the light fixture, the cable configured to raise or lower the light fixture.

5. The apparatus of claim 1, further comprising a first bar pivotably coupled to the light fixture and a support, the first bar configured to cause the light fixture to rotate when the actuator raises or lowers the light fixture.

6. The apparatus of claim 1, further comprising an inspection booth having a ceiling, the actuator coupled to the inspection booth to suspend the light fixture inside the inspection booth below the ceiling.

7. A system, comprising:
   a first array of first light fixtures;
   a second array of second light fixtures; and
   an actuator operatively coupled to the second array of second light fixtures to move the second array of second light fixtures from a first position to a second position, the second array of second light fixtures offset from the first array of first light fixtures to enable the second light fixtures to interlace the first light fixtures when the second array of second light fixtures moves from the first position to the second position.

8. The system of claim 7, wherein longitudinal axes of the first light fixtures are substantially parallel.

9. The system of claim 7, where the first array of first light fixtures is disposed above the second array of second light fixtures when the second array of second light fixtures is in the first position.

10. The system of claim 7, wherein the second light fixtures are interlaced with the first light fixtures when the second array of second light fixtures is in the second position.

11. The system of claim 10, wherein the actuator is operatively coupled to the second array of second light fixtures at a position spaced apart from a center of mass of the second array of second light fixtures.

12. The system of claim 7, further comprising a cable operatively coupling the actuator to the second array of second light fixtures.

13. The system of claim 12, further comprising a bar pivotably coupled to the second array of second light fixtures, the bar configured to guide a rotational path of the second array of second light fixtures.

14. An apparatus, comprising:
   a light fixture;
   a cable operatively coupled to the light fixture;
   an actuator operatively coupled to the cable to at least one of draw in or draw out the cable; and
   a bar having a first portion and a second portion, the first portion pivotably coupled to the light fixture, the second portion to be pivotably coupled a support.

15. The apparatus of claim 14, further comprising a first beam supporting the light fixture, the cable coupled to the first beam.

16. The apparatus of claim 15, further comprising a second beam supporting the light fixture, the bar pivotably coupled to the second beam to pivotably couple to the light fixture.

17. The apparatus of claim 16, wherein the second beam is coupled to the light fixture adjacent an end of the light fixture.

18. The apparatus of claim 14, wherein the cable and the bar are spaced apart to enable the bar to rotate the light fixture when the actuator at least one of draws in or draws out the cable.

19. The apparatus of claim 14, wherein the support is a structural support of an inspection booth.

20. The apparatus of claim 14, wherein the actuator comprises a winch.

* * * * *